United States Patent

Cutié et al.

[11] Patent Number: 5,120,846
[45] Date of Patent: Jun. 9, 1992

[54] PROCESS FOR PREPARING PHOSPHOROTHIOATES AND PHOSPHONOATES IN A THREE-PHASE SYSTEM

[75] Inventors: Zonia G. Cutié, Midland, Mich.; Marc E. Halpern, Cherry Hill, N.J.

[73] Assignee: DowElanco, Indianapolis, Ind.

[21] Appl. No.: 537,315

[22] Filed: Jun. 13, 1990

[51] Int. Cl.$^5$ ............ C07F 9/58; C07F 9/6509; C07F 9/6512; C07F 9/12; C07F 9/40
[52] U.S. Cl. .................. 546/25; 544/243; 544/337; 558/98; 558/100
[58] Field of Search ............ 546/25; 544/243, 337; 558/100, 98

[56] References Cited

U.S. PATENT DOCUMENTS

| | | | |
|---|---|---|---|
| 3,928,370 | 12/1975 | Wang et al. | 260/297 |
| 4,007,197 | 2/1977 | Freedman et al. | 546/25 |
| 4,016,225 | 4/1977 | Kroposki et al. | 558/100 |
| 4,028,439 | 6/1977 | Kroposki et al. | 558/100 |
| 4,147,866 | 4/1979 | Freedman et al. | 544/243 |
| 4,814,448 | 3/1989 | Gatling et al. | 546/25 |
| 4,814,451 | 3/1989 | Gatling | 546/25 |

*Primary Examiner*—Robert T. Bond
*Assistant Examiner*—E. Bernhardt
*Attorney, Agent, or Firm*—Alice A. Brewer

[57] ABSTRACT

The present invention is directed to the preparation of certain phosphorothioates and phosphonates by means of a process which employs a three-phase system for the reaction of an alkali metal or alkaline earth metal phenate, pyridinate or pyrimidinate with a phosphorochloridothioate or phosphorochloridate under alkaline conditions and in the presence of tertiary amine and quarternary ammonium salt co-catalyst, but in the absence of both a hydrocarbon or chlorinated hydrocarbon solvent and a surfactant.

10 Claims, No Drawings

PROCESS FOR PREPARING PHOSPHOROTHIOATES AND PHOSPHONOATES IN A THREE-PHASE SYSTEM

BACKGROUND OF THE INVENTION

A number of phosphates and phosphorothioates were described by Rigterink in U.S. Pat. No. 3,244,586. Such compounds are particularly useful as insecticides and biocides. They are represented by Formula I.

$$R-O-\underset{\underset{R'}{|}}{\overset{\overset{Z}{\|}}{P}}-R' \qquad (I)$$

wherein R represents halopyridyl, Z represents oxygen or sulfur and each R' independently represents lower alkyloxy, amino or lower alkylamino.

Rigterink disclosed several methods for preparing the compounds but his preferred method comprised reacting a phosphorochloridate or phophorochloridothioate of Formula II $$Cl-\underset{\underset{R'}{|}}{\overset{\overset{Z}{\|}}{P}}-R' \qquad (II)$$

with an alkali metal or tertiary amine salt of a halopyridinol having the formula R—O-alkali metal or R—OH tertiary amine. The disclosed methods are carried out in an inert organic liquid under anhydrous conditions. In each of the disclosed processes, an alkali metal chloride or the tertiary amine hydrochloride salt is produced as a reaction byproduct which is removed by filtration. The disclosure of U.S. Pat. No. 3,244,586 is incorporated herein by reference.

Other phosphorothioates and phenylphosphonothioates have been similarly prepared and used. See, for example, U.S. Pat. Nos. 4,007,197, and 4,147,866 both of which teach the reaction of an alkali metal phenate, pyridinate or pyrimidinate with an O,O-dialkylphosphorochloridothioate or O-alkyl phenylphosphonochloridothioate under alkaline conditions in a hydrocarbon or chlorinated hydrocarbon solvent reaction medium and in the presence of a co-catalyst mixture of a quarternary ammonium or phosphonium salt and a tertiary amine.

U.S. Pat. No. 3,928,370 teaches the preparation of dialkyl pyridylphosphates by the reaction of an alkali metal pyridinate and a dialkyl hydrogen phosphite in the presence of a liquid reaction medium and in the presence of a tertiary amine catalyst.

U.S. Pat. No. 4,814,448 teaches the preparation of phosphorothioates and phosphates by the reaction of an alkali metal or alkaline earth metal phenate, pyridinate or pyrimidinate with a phosphorochloridothioate or phosphorochloridate in an alkaline aqueous hydrocarbon or chlorinated hydrocarbon solvent system in the presence of a tertiary amine catalyst and a nonionic surfactant. U.S. Pat. No. 4,814,451 teaches a similar process but with the absence of hydrocarbon or chlorinated hydrocarbon solvent.

Many other commercially available phosphorothioates and phosphates prepared by the same general procedure as set forth above are listed in articles by O. Johnson in *Chemical Week*, pp. 10-46 (Jul. 26, 1972), and by E. E. Kenaga and W. E. Allison in the *Bulletin of the Entomological Society of America*, 15(2), pp. 85-148 (Jun. 1969) which also list the U.S. Patent Numbers of many of said compounds. These articles are incorporated herein by reference thereto.

SUMMARY OF THE INVENTION

The present invention is directed to the preparation of certain phosphorothioates and phosphonoates in high yields and of high purity by a process which employs a three-phase system for the reaction of an aklali metal or alkaline earth metal phenate, pyridinate or pyrimidinate with a phosphorochloridothioate or phosphorochloridate under alkaline conditions and in the presence of tertiary amine and quarternary ammonium slat cocatalysts, but in the absence of a hydrocarbon or chlorinated hydrocarbon solvent and in the absence of a nonionic surfactant.

The compounds prepared by the process of the present invention correspond to the general formulae $$R-O-\overset{\overset{Z}{\|}}{P}-(OR')_2 \qquad (III)$$

or $$R-O-\overset{\overset{Z}{\|}}{P}\overset{R'}{\underset{OR'}{\diagdown}} \qquad (IV)$$

wherein
R is and
each R' independently represents C$_1$-C$_6$ alkyl, phenyl, phenyl mono- or di-substituted by fluoro, chloro, bromo, methyl or ethyl or any combination thereof, pyridyl or pyridyl mono- or di-substituted by fluoro, chloro, bromo, methyl of ethyl or any combination thereof;

each X independently represents bromo, chloro, fluoro, iodo, —NR$^2$R$^3$, cyano, nitro, C$_1$-C$_6$ alkyl, C$_1$-C$_6$ alkoxy, C$_1$-C$_6$ alkylthio or C$_1$-C$_6$ alkylsulfinyl;

R$^2$ and R$^3$ each independently represent hydrogen or C$_1$-C$^6$ alkyl;

n is 0, 1, 2, or 3 with the proviso that when n is more than one, all the ring substituents are mutually sterically compatible; and Z is oxygen or sulfur.

An advantage of the present invention is the production of the above-indicated products in high yields and in high purity and at an acceptable rate in the absence of both solvent and surfactant, and with reduced amounts of such impurities as starting unreacted material or byproduct such as tetraethyl dithiopyrophosphate, also known as sulfotepp.

The term "C$_1$-C$_6$ alkyl", as used herein, means straight chain alkyls of from 1 to 6 carbon atoms, branched chain alkyls of 3 to 6 carbon atoms and cyclic alkyls of 3 to 6 carbon atoms such as, for example, methyl, ethyl, propyl, butyl, isopropyl, isobutyl, secondary butyl, tertiary butyl, cyclopropyl, cyclobutyl, amyl and cycloamyl.

The terms "$C_1$-$C_6$ alkoxy", "$C_1$-$C_6$ alkylthio", "$C_1$-$C_6$ alkylsulfinyl", and $C_1$-$C_6$ alkylsulfonyl" mean groups of the formula

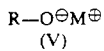

wherein Y is oxygen, sulfur, sulfinyl or sulfonyl and alkyl is defined as hereinabove set forth for "$C_1$-$C_6$ alkyl."

In the present specification and claims, the term "mutually sterically compatible" means X substituent groups which are not affected by steric hindrance. Steric hindrance is defined in The Condensed Chemical Dictionary, 7th Edition, Reinhold Publishing Co. N.Y., page 893 (1966) as follows:

"A characteristic of molecular structure in which the molecules have a spatial arrangement of their atoms such that a given reaction with another molecule is prevented or retarded in rate."

Steric hindrance may be further defined as compounds having substituents whose physical bulk does not require confinement within volumes insufficient for the exercise of their normal behavior as discussed in *Organic Chemistry* of D. J. Cram and G. Hammon, 2nd Ed., McGraw-Hill Book Co., N.Y., page 215 (1964).

In the process of this invention, the compounds of Formulae III and IV are prepared by reacting under alkaline conditions at a pH of from about 7 to about 13, preferably at a pH of about 9 to about 11, in the presence of a catalytic amount of a tertiary amine, and in the presence of a quarternary ammonium additive, substantially equimolar amounts or an excess of Reactant (a) of the formulae $$R-O^{\ominus}M^{\oplus} \quad \text{(a)}$$
$$(V)$$

wherein M represents an alkali metal cation or alkaline-earth metal cation when taken together with a superscribed $\oplus$ symbol;
with a phosphorochloridate or phosphorochloridothioate
Reactant (b) of one of the formulae

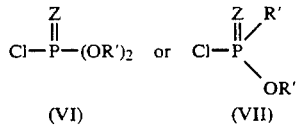

The reaction takes place in a three-phase system, one phase being primarily a mixture of Reactant (b), that is, a compound of Formula VI or VII, and the tertiary amine catalyst and quarternary ammonium additive, the second phase being an aqueous reaction medium comprising water, a buffer mixture capable of maintaining a pH in the aqueous reaction medium in the range of about 7 to about 13 during the course of the reaction, and Reactant (a), that is, a compound of Formula V, and a third phase being excess solid Reactant (a).

In carrying out the reaction process of this invention, the phenate, pyridinate or pyrimidinate salt (Reactant (a)) selected and the phosphorochloridate or phosphorochloridotioate (Reactant (b)) are mixed and contacted together in any convenient fashion, and the resulting mixture maintained for a period of time at a temperature in the range of from about 0° to about 100° C., preferably at about 45° to 75° C., to complete the reaction. In order to ensure high yields of the desired reaction product and low sulfotepp contamination, an excess of the Formula V (Reactant (a)) is used. The reaction pressure is not critical and generally atmospheric pressure is used as a matter of convenience. Under the above conditions, reaction times of up to 4 hours are common, although reaction times of from 0.5 hours to 2 hours generally are sufficient for the reaction to be substantially complete.

The term "alkali metal", as used herein, means sodium, potassium, rubidium, lithium and cesium. The term "alkaline earth metal", as used herein, means calcium, strontium, barium, radium, and magnesium.

The tertiary amines used in this process are used in small but catalytic amounts. For example, amounts of from about 0.05 to about 5 mol percent, based on the mols of alkali metal, or alkaline earth metal, phenate, pyridinate or pyrimidate reactant employed, are suitable tertiary amines, but amounts of from about 0.1 to about 1.0 mol percent are generally preferred. Examples of suitable tertiary amines include aliphatic trihydrocarbyl amines such as trimethylamine, ethyldimethylamine, butyldimethylamine, N,N,N',N'-tetramethylethylenediamine, and the like; aliphatic heterocyclic amines such as 1-azabicyclo[2.2.2]octane, 1-methyl-2-imidazoline, 1-methylpyrolidine, and the like mixed aliphatic/aromatic amines such as 4-(N,N-dimethylamino)pyridine, 4-(N-pyrrolidino)pyridine, phenyldimethylamine, and the like; and other like organic, sterically unhindered, nucleophilic, tertiary amines.

The quarternary ammonium additives used in this process are used in catalytic amounts. Examples of quarternary ammonium additives suitable for use in this invention include pentyltrimethylammonium, heptyltrimethylammonium and hexyltrimethylammonium chloride. Amounts of about 0.05 mol percent to about 5 mol percent relative to the amount of Reactant (b) employed, are effective, and quantities of from about 0.1 mol percent to about 3.0 mol percent are preferred.

Other quarternary ammonium additives may also be employed in this process, such as ammonium chloride, benzyltrimethylammonium and ($C_1$-$C_7$)alkyltri($C_2$-$C_8$ alky)ammonium compounds such as ethyltributylammonium chloride. However, to be effective, the quantities of these additives generally must be greater than that of the pentyl-, hexyl- and heptyltrimethylammonium additives described above. For example, quantities of about 3 mol percent to about 10 mol percent relative to the Reactant (b) employed are effective, and quantities of from about 5 mol percent to about 8 mol percent are preferred. It should be noted that the use of butyltrimethylammonium is undesirable in that it results in unacceptably high sulfotepp impurity, and the use of octyltrimethylammonium and the ($C_9$-$C_{18}$)alkyltrimethylammonium membezs of the series are undesirable in that they result in post reaction emulsions.

The alkaline conditions under which this reaction is carried out can be easily achieved by conducting the process in the presence of caustic (NaOH) or caustic potash (KOH) or other conventional base. The specific base employed is, in general, not critical and the main limitation on the base used is that it not unfavorably react with the reactants to prevent the desired reaction from taking place.

Vigorous agitation of the reaction mixture, for example by stirring or swirling, is especially important since this process is conducted in a three-phase reaction medium.

The desired product can be separated from the reaction product of the above preparative procedures employing conventional separatory procedures known to those skilled in the art including steps such as, for example, solvent extraction, filtration, water washing, column chromatography, neutralization, acidification, crystallization and distillation.

An advantage of the present invention is that it provides a method of making the desired products in the substantial or preferably complete absence of any surfactant or solvent. This as well as the presence of the co-catalysts, that is, the tertiary amine and the quarternary ammonium salt, present the advantage of eliminating the use of an organic solvent medium and the use of a surfactant while nevertheless achieving the above-indicated products in high yields and high purity with low levels of sulfotepp impurity and with the elimination of emulsions which may exist at the end of the esterification reaction as a result of the use of surfactants, thereby also eliminating the need for time consuming and special processing necessary when emulsions are present.

Since the compound preparation procedures disclosed herein employ only standard chemistry practices and it is known that slightly different reactants can require slightly different reaction parameters from those for other reactants, it is to be understood that minor modifications to the reaction parameters set forth such as the use of an equivalent solvent, the use of an excess of one of the reactants, the use of a catalyst, the use of high temperature and/or pressure equipment, high speed mixing and other such conventional changes are within the scope of this invention.

The following examples illustrate the present invention and the manner by which it can be practiced, but, as such, should not be construed as limiting the overall scope of this invention in any way.

EXAMPLE 1

Preparation of Chlorpyrifos, i.e., O,O-diethyl-O-(3,5,6-trichloro-2-pyridyl)phosphorothioate Into a glass reactor equipped with an agitator set at 900 rpm fitted with two stirring impellers separated by 2.5 inches, pH control set at 10.6, and heat control set at 60° C., were placed the following: 1440 g of hydrolysate containing 20 wt % sodium trichloropyridonate, 6 wt % NaCl, 10 wt % NaOH and the rest water; in addition, 70 g of 10% aqueous NaCl and 1.0 ml of 55.1% aqueous hexyltrimethylammonium chloride. The pH was adjusted to 10.6 by the addition of aqueous HCl and 5.5 ml of 2.9 wt % aqueous 4-(N,N-dimethylamino)pyridine was added to the mixture at 60° C. Diethylphosphorochloridothioate (180 ml) during four minutes and 30 seconds. Fourteen minutes after the beginning of the addition of the diethylphosphorochloridothioate, 2.6 ml of 2.9 wt % aqueous 4-(N,N-dimethylamino)pyridine was added. After a total reaction time of 46 minutes, the chlorpyrifos product was recovered by filtering off unreacted starting material and separating the organic and aqueous layers using a separatory funnel. The organic, or product, layer was immediately washed once with water and dried. The title product was recovered in 95.5% yield, containing 0.14% sulfotepp, only 1.2% diethylphosphorochloridothioate.

EXAMPLE 2

Preparation of Chlorpyrifos, i.e., O,O-diethyl-O-(3,5,6-trichloro-2-pyridyl)phosphorothioate To the reactor described in Example 1 were added the following: 270 g of powder containing 85.4 wt % sodium trichloropyridonate and 14.6 wt % water, 60.8 g NaCl, 850 ml water, and 12.0 ml of 55.1 wt % aqueous hexyltrimethylammonium chloride. The mixture was heated to 59° C. and the stirrer set at 1000 rpm and the pH control set at 10.4. To the mixture were added 17.0 ml of 1.0 wt % aqueous 4-(N,N-dimethylamino)pyridine, then 160 ml diethylphosphorochloridothioate. After 120 minutes, the reaction mixture was filtered, the layers separated, and the title product collected in 97.0% yield, containing 0.17% sulfotepp and 0.30% diethylphosphorochloridothioate.

It should be apparent to one of ordinary skill in the art that changes and modifications can be made to this invention without departing from the spirit or scope of the invention as it is set forth herein.

What is claimed is:

1. A process for preparing a compound corresponding to one of the formulae

(III)

or

(IV)

wherein
R is

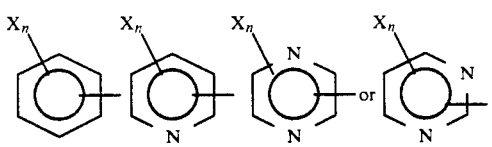

and each R' independently represents $C_1$-$C_6$ alkyl, phenyul, phenyl mono- or di-substituted with fluoro, chloro, bromo, methyl or ethyl or any combination thereof, pyridyl or pyridyl mono- or di-substituted by fluoro, chloro, bromo, methyl or ethyl or any combination thereof;

each X independently represents bromo, chloro, fluoro, iodo, —$NR^2R^3$, cyano, nitro, $C_1$-$C_6$ alkyl, $C_1$-$C_6$ alkoxy, $C_1$-$C_6$ alkylthio or $C_1$-$C_6$ alkylsulfinyl;

$R^2$ and $R^3$ each independently represent hydrogen or $C_1$-$C_6$ alkyl;

n is 0, 1, 2, or 3 with the proviso that when n is more than one, all the ring substituents are mutually sterically compatible; and Z is oxygen or sulfur, which consists essentially of reacting, under alkaline conditions, Reactant (a) corresponding to the formulae $$R-O^{\ominus}M^{\oplus} \quad (a)$$
$$(V)$$

wherein

M represents an alkali metal cation or alkaline-earth metal cation;

with Reactant (b) corresponding to one of the formulae

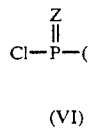 or 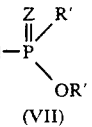     (b)

(VI)        (VII)

in the presence of a catalytic amount of a tertiary amine, and in the presence of a quarternary ammonium additive; the reaction being carried out in a three-phase system, one phase being primarily the Reactant (b), said tertiary amine catalyst and said quarternary ammonium additive, a second phase being an aqueous reaction medium maintaining a pH in the aqueous reaction medium in the range of about 7 to about 13 during the course of the reaction, and the Reactant (a), and a third phase being excess solid Reactant (a), said reaction being carried out in the absence of a surfactant, and in the absence of an organic solvent.

2. The process according to claim 1 wherein the quarternary ammonium additive is hexyltrimethylammonium chloride.

3. The process according to claim 1 wherein the compound prepared is compound of the formula $$\underset{\underset{\parallel}{R-O-P-(OR')_2}}{\overset{Z}{}} \quad (III)$$

4. The process according to claim 2 wherein the compound prepared is compound of the formula $$\underset{\underset{\parallel}{R-O-P-(OR')_2}}{\overset{Z}{}} \quad (III)$$

5. The process according to claim 1 wherein the compound prepared is compound of the formula

     (IV)

6. The process according to claim 4 wherein R is

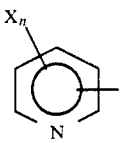

and R' is $C_1$–$C_6$ alkyl.

7. The process according to claim 6 wherein R is 3,5,6-trichloro-2-pyridyl and R' is methyl or ethyl.

8. The process according to claim 7 wherein R' is ethyl.

9. The process according to claim 4 wherein the Reactant (a) is sodium O-3,5,6-trichloro-2-pyridinate and the Reactant (b) is O,O-diethylphosphorodichloridothioate.

10. A process according to claim 9 wherein unreacted Reactant (a) of the formula $R\text{-}O^{\ominus}M^{\oplus}$ is removed from the reaction mixture by filtration, the organic and aqueous layers are separated, and the organic layer is retained and washed.

* * * * *